United States Patent [19]

Chaudhari et al.

[11] Patent Number: 4,681,858
[45] Date of Patent: Jul. 21, 1987

[54] DISSOLUTION CELL AND METHOD FOR DETERMINING THE IN-VITRO RELEASE OF A DRUG

[75] Inventors: Atma Chaudhari, West Hill; Joseph K. S. Lee, Agincout, both of Canada

[73] Assignee: Warner-Lambert Company, Morris Plains, N.J.

[21] Appl. No.: 940,708

[22] Filed: Dec. 11, 1986

[30] Foreign Application Priority Data

Jun. 19, 1986 [CA] Canada ................................. 511997

[51] Int. Cl.⁴ ...................... B01D 11/02; G01N 1/00; G01N 33/15; G01N 37/00
[52] U.S. Cl. ................................ 436/165; 73/863.23; 73/866; 422/68; 422/270; 422/277
[58] Field of Search ............... 422/266, 270, 274, 275, 422/276, 277, 68; 73/866, 863.23; 424/2; 436/34, 165

[56] References Cited

U.S. PATENT DOCUMENTS 3,595,623 7/1971 Sperti .................................. 422/276
3,802,272 4/1974 Bischoff et al. ..................... 73/866
4,108,602 8/1978 Hanson et al. ........................ 73/866
4,279,860 7/1981 Smolen .................................. 73/866

OTHER PUBLICATIONS

Garrett et al., J. Pharm. Sci., V. 57, No. 6, 1968, pp. 944-948.

Primary Examiner—Barry S. Richman
Assistant Examiner—C. M. Delahunty
Attorney, Agent, or Firm—Gary M. Nath

[57] ABSTRACT

The invention provides a dissolution cell and method for determining the in-vitro release rate of a drug in suitable form, e.g. a suppository. The cell includes a solid rectangular top wall and a pair of trapezoidal side walls extending from the top wall. Disposed between the side walls are a pair of end walls and a bottom wall each comprised of a wire mesh material. The bottom wall and end walls can be made in one piece. The top wall has an opening and a flanged extension which can be coupled to a suitable rotating device. In use the cell containing the drug is rotated in a suitable dissolution medium and the rate of release of the drug is determined by analyzing the amount of drug released to the dissolution medium at predetermined intervals.

13 Claims, 6 Drawing Figures

DISSOLUTION CELL AND METHOD FOR DETERMINING THE IN-VITRO RELEASE OF A DRUG

BACKGROUND OF THE INVENTION

This invention is concerned with a dissolution cell and method for determining the in-vitro release of a drug in suitable form.

After rectal administration of a suppository, the in-vivo release of the drug contained in the base is sometimes irregular and incomplete which, among other reasons, is due to poor release of the drug from the suppository. The drug release characteristics, in general, are greatly influenced by the type of base and the excipients used in the suppository formulations. The dissolution property of the drug itself can also be an important factor in determining the in-vivo and/or in-vitro release of drug from the suppository.

One basic problem in testing for drug release from a suppository is that the suppository softens, deforms, melts, or disintegrates during the test, exposing a variable interfacial area to the dissolution medium. Because the release rate is dependent on this interfacial area, the variability of this factor leads to poor test reproducibility.

Many investigators have tried a number of approaches to study the correlation between in-vitro and in-vivo release of a drug from suppositories. The methods so far available for in-vitro dissolution testing, in general, are lacking in universal acceptance and reproducibility and are difficult to perform. As a result, no single method or device has emerged as a standard procedure for studying pharmaceutical availability of a drug administered in suppository form. Furthermore, no officially recognized dissolution test for suppositories has been mandated yet by any regulatory agencies.

The methods available for studying the in-vitro release rate of suppositories can be classified in terms of five general types.

The first type consists of placing a suppository in a beaker containing a dissolution medium, e.g. phosphate buffered solution, and supporting the suppository with wire or pins at both ends. A stirrer is immersed in the beaker to allow the dissolution medium to circulate about the suppository. Release of drug is determined by taking up samples of the dissolution medium and analyzing their content spectrophotometrically. See for example Biopharmaceutics of Aminophylline Suppositories, C. J. de Blaey and J. J. Rutten—Kingma Pharm. Acta. Helv. 52. Nr. ½ (1977). This method is not effective since the suppository floats on top of the dissolution medium and dissolution is not uniform.

The second type utilizes the USP dissolution wire basket for holding the suppository. The USP dissolution wire basket consists of a cylindrical container made primarily of wire mesh and open at the end for insertion of the suppository. It is suspended in the dissolution medium and rotated. The medium flows through the mesh material and contacts the suppository. Release of drug is determined spectrophotometrically. The disadvantage of this method is that the mesh material of the basket becomes clogged with the suppository composition base material, e.g. wax, which affects the release rate measurement.

The third type employs a membrane in a diffusion cell, wherein a receiver compartment is separated from a donor compartment by a membrane across which the released drug migrates. The donor compartment separated by the membrane is equipped with a port for introducing a drug sample to be tested for release rate, e.g. a suppository and a stirrer. The receiver compartment is also equipped with a stirrer and a sample port for removal of released sample. Both compartments contain a dissolution medium, e.g. phosphate buffer having a pH approaching that of the rectal area. See for example E. R. Garrett and P. B. Chemburkar, J. Pharm. Sci. 57(6), 944 1968. Membranes have been considered more suitable in release rate studies on the assumption that the interfacial area of the suppository would be controlled as the softened mass of suppository would spread over the entire membrane. However, the introduction of an additional physical process, i.e. membrane transport, can complicate matters and may mask the real release characteristics for certain drug-suppository base combinations. Another disadvantage of this procedure is that it employs compartments which are only 9 ml. in volume. Thus when samples are taken for measurement only a limited liquid volume remains for further sample removal.

In the fourth method for studying release rate of suppository, the suppository is placed in a dialysis tube, its both ends tied and then placed in the dissolution medium. Samples of the dissolution medium are taken periodically to determine the amount released. See J. J. Tukker and C. J. de Blaey Acta. Pharma. Tech. 29(2) 131 (1983).

In the fifth method a continuous flow system instrumental set up is employed. The apparatus consists of a glass bead-bed containing the suppository. A continuous flow of liquid is passed through the bead-bed at a constant rate. Direct contact of the suppository is maintained with the dissolution medium confining the suppository within the beads. See for example T. J. Roseman, et al, J. Pharm. Sci. Vol. 70, No. 6, June 1981.

The present invention, on the other hand, provides a simple and effective dissolution cell for determining drug release in-vitro. This cell allows the suppository to disperse in the dissolution medium and provides reproducible release rate data.

Experiments using this device gave good reproducibility and thus helped find in-vitro release rate and rank order for various formulations. Because the cell allows simple, quick and reproducible results, it can be applied to study the effect of formulation differences on drug release for suppository categories of products.

SUMMARY OF THE INVENTION

In brief, the invention provides a boat-shaped dissolution cell and method for the determination of the in-vitro release of a drug from a carrier, such as a suppository into a dissolution medium and method using said cell.

The cell comprises a rectangular top wall having a central opening for receiving the drug. Extending from the top wall are a pair of trapezoidal side walls, the top wall and side walls being made of solid metal. A pair of end walls and a bottom wall comprised of a mesh material extending between the side walls, the end walls and bottom wall preferably being made of a single unit of mesh material. A circular flanged extension extends upwardly from the opening which can be connected with the shaft of a stirring apparatus.

To perform the method of the invention, the drug in suitable form, e.g. a suppository, is placed in the cell and it is immersed in a dissolution medium such as a phosphate buffered solution having a pH approximating that of the medium under consideration, e.g. rectal pH. The cell, coupled to a stirring apparatus, is rotated and over predetermined intervals, samples of the dissolution medium are withdrawn and analyzed for the concentration of drug released therein. The meshed end walls and bottom wall allow free access of the medium to the cells thereby promoting uniform release. In addition, the solid side walls act as paddles to cause turbulence of the medium.

DETAILED DESCRIPTION OF THE PREFERRED EMBODIMENTS

Referring to FIGS. 1 to 6 there is shown a rotating dissolution cell according to the invention indicated generally by 11.

Figure 1:
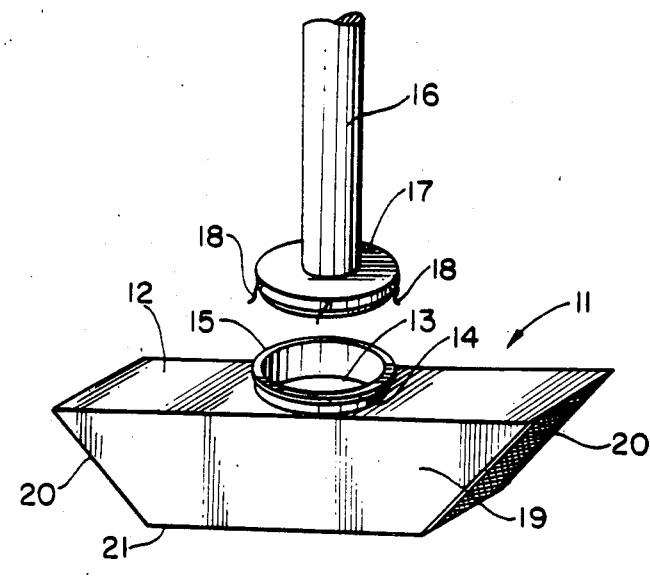
FIG. 1 is a perspective view of the rotating dissolution cell of the invention.
Figure 2:
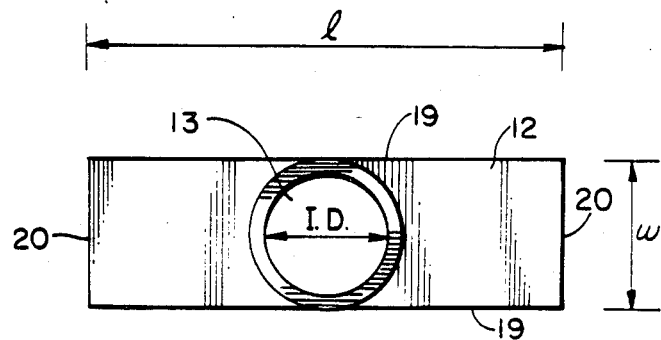
FIG. 2 shows a plan view of the cell.
Figure 3:
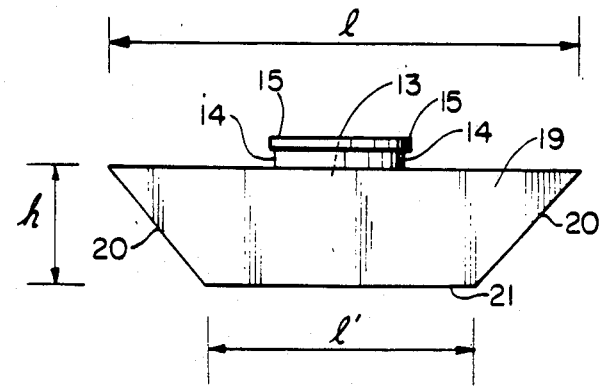
FIG. 3 shows a side elevation view of the cell.
Figure 4:
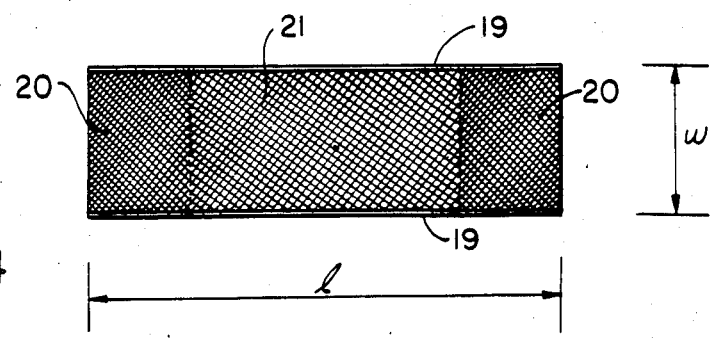
FIG. 4 shows a bottom view of the cell.
Figure 5:
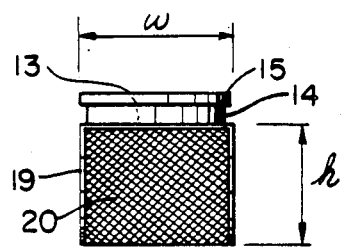
FIG. 5 shows an end view of the cell.
Figure 6:
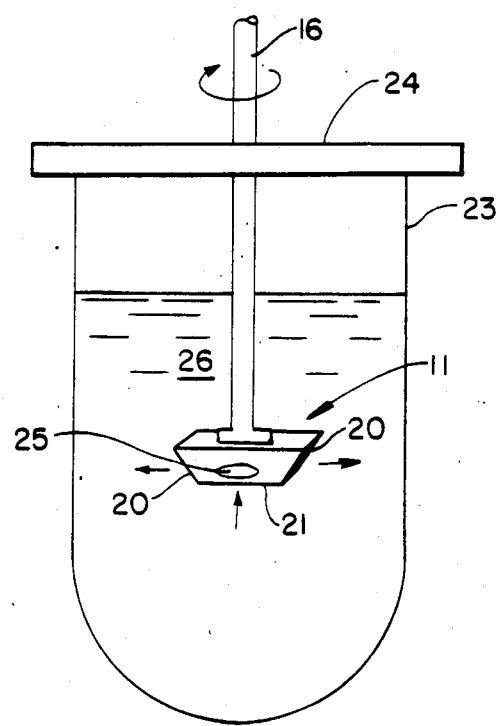
FIG. 6 shows the rotating dissolution cell of the invention in a USP dissolution vessel.

The cell consists of a boat-shaped container for a drug in capsule or other drug form having solid metal and metal mesh walls; the metal being preferably stainless steel to obviate corrosion problems. The top wall 12 is comprised of solid metal of rectangular shape having a length l and width w. The top wall has a central circular opening 13 having an inner diameter (I.D.) for introduction of the drug. Bounding opening 13 is circular extension 14 terminating in circular flange 15. Disposed above the extension and flange is dissolution shaft 16 having mounted at its terminus coupling 17. Circumferentially spaced about coupling 17 are clips 18. These clips are adapted to engage the rim of flange 15 to releasably secure the coupling and shaft thereto as shown in FIG. 6. The shaft 16 is in turn coupled to a means for rotating the shaft such as a motor or other rotating device. The cell 11 further consists of solid metal side walls 19 of trapezoidal configuration having common length l with top wall 12, short length l'; and height h. Disposed bettween the side walls are end walls 20 preferably made of stainless steel wire mesh having width w. The cell is completed by bottom wall 21 also preferably comprised of stainless steel wire mesh having length l' and width w. The end walls 20 and bottom wall 21 are preferably made of one piece of wire mesh material. The preferred wire mesh material is a 30 mesh stainless steel wire screen wherein the wire diameter is 0.013 inches.

Although it is not critical to the invention the following dimensions have been shown to be suitable for the cell. The length l of the top wall 12 and side walls 19 should be about 8 cm. and the width w of the top wall, end walls 20 and bottom wall 21 should be about 2.5 cm. The short length l' of the side walls 19 and bottom wall 21 should be about 4.5 cm. The height h of the side walls 19 and end walls 20 should be about 2.0 cm. The inner diameter (I.D.) of the central opening should be about 2.0 cm.

In use, a drug form 25, e.g. a suppository is introduced into the cell through opening 13 and the cell 11 is coupled to the dissolution shaft 16 which is in turn connected with a means for rotating the shaft as shown in FIG. 6. The cell is immersed in a USP dissolution vessel 23 having cover 24. The dissolution vessel contains an aqueous phosphate buffer solution 26 maintained at a pH of 7.8 and at a temperature of 37° C. for example to approximate the rectal environment. The cell is immersed centrally in the solution 26 about 2.5 cm. from the bottom of the vessel 23. The cell is then rotated at a fixed speed and samples of the dissolution medium are removed and analyzed spectrophotometrically for drug concentration. It has been found that circulation of the solution occurs through the bottom wall 21 and out the side walls 20 as shown by the arrows in FIG. 6 at a uniform rate and that no clogging of the mesh occurs as in the USP basket. The meshed end walls and bottom walls allow free access of the medium to the cell and the flat side walls function as paddles to stir the medium. In this manner, release of the drug in-vitro can be accurately determined.

In order to more fully describe the present invention, the following Examples are provided. The Examples illustrate particular application of the rotating cell of the invention but are not deemed to limit the scope of the invention.

EXAMPLE 1

In this Example, a USP rotating basket was employed to determine the dissolution release rate of an anti-arthritic drug from a 600 mg. suppository. The dissolution wire basket consisted of a cylindrical wire mesh container into which the suppository was inserted. It was suspended in a standard phosphate buffer solution at 37° C. having a pH of about 7.8 to approximate the rectal pH and rotated. A Reference Standard solution of anti-arthritic drug in the dissolution medium was also prepared. Two experiments were conducted in which the basket was rotated at 50 rpm and 100 rpm.

At one half hour intervals, samples were withdrawn with a pipette fitted with glass wool plug from about the center portion of the dissolution medium.

Using a spectrophotometer, the absorbance of the Reference Standard (As) and sample (Au) at 272 nm was measured agaist the phosphate buffer solution 7.8, as blank.

TABLE 1

| Time (Hours) | 50 RPM % Release | 100 RPM % Release |
| --- | --- | --- |
| 0.5 | 10.3 | 14.8 |
| 1.0 | 13.7 | 20.0 |
| 1.5 | 17.0 | 24.8 |
| 2.0 | 24.1 | 29.4 |
| 2.5 | — | 33.6 |
| 3.0 | — | 37.3 |
| 3.5 | — | 40.6 |
| 4.0 | — | 45.1 |
| 6.0 | — | — |
| 8.0 | — | — |

It was noted that the suppository base clogged the mesh in the basket and hindered the release rate of the drug. The increase in the stirring speed from 50 to 100 rpm did not significantly improve the release rate of the drug.

EXAMPLE 2

In this Example the dissolution release rate of the anti-arthritic drug in the suppository of Example 1 was determined using the basket method of Example 1 and also dialyzer tubing having a 12,000 Molecular Weight Cut Off (MWCO 12,000 and 50,000). In each case the suppository was inserted in the dialyzer tubing with 3.7 ml of pH 7.8 phosphate buffer, both ends were tied and placed in the basket.

Table 2 summarizes the results.

TABLE 2

| Time (Hours) | 12,000 MWCO % Drug Released | 50,000 MWCO % Drug Released |
|---|---|---|
| 0.5 | — | — |
| 1.0 | — | — |
| 1.5 | — | — |
| 2.0 | 13.6 | 11.3 |
| 2.5 | — | — |
| 3.0 | — | — |
| 3.5 | — | — |
| 4.0 | 20.7 | 18.3 |
| 6.0 | 27.4 | 24.6 |
| 8.0 | 33.8 | 30.0 |
| 10.0 | 40.0 | 34.4 |
| 12.0 | 45.0 | 38.5 |
| 14.0 | 50.0 | 42.5 |
| 16.0 | 54.0 | 46.1 |

As Table 2 shows the dialyzer tubing lowered the release rate of the drug compared to Example 1.

EXAMPLE 3

In this Example the rotating boat-shaped dissolution cell as described in FIGS. 1-6 was employed to determine the release rate of the anti-arthritic drug suppository of Example 1.

About 600 ml of prepared degased dissolution medium was placed in each of six dissolution vessels, and the dissolution medium was warmed to 37°±0.5° C. One suppository was placed in each of the six rotating boat-shaped dissolution cells, and then were lowered into their respective vessels, maintaining the distance between the inside bottom of the vessel and the bottom of the cell at 2.5±0.2 cm during the test.

Table 3 shows the Mean % Dissolution Release Rate in minutes for the suppositories at 60, 80, 100, 120 and 150 rpm (150 rpm repeated three times).

TABLE 3

| No. of Cells | RPM | Mean % Dissolution Release Rate (Minutes) | | | | | | |
|---|---|---|---|---|---|---|---|---|
| | | 15 | 20 | 30 | 45 | 60 | 75 | 90 |
| 1 | 60 | — | — | 13.9 | 19.5 | 21.6 | — | — |
| 1 | 80 | — | — | — | — | 63.4 | 65.3 | 68.8 |
| 3 | 80 | 19.2 | — | 35.1 | 43.7 | 50.4 | — | 60.0 |
| 6 | 100 | — | — | — | 59.1 | 67.1 | 79.4 | — |
| 6 | 120 | 36.8 | — | 79.2 | 92.0 | 95.7 | — | — |
| 6 | 150 | — | — | 92.7 | — | — | — | — |
| 6 | 150 | 68.2 | 78.9 | 90.0 | — | — | — | — |
| 6 | 150 | 80.2 | — | 98.5 | — | — | — | — |

For method validation purposes the dissolution release data on the same suppository was obtained at a stirring speed of 120 rpm by repeating the conditions three times. These data showed good reproducability with the standard deviation remaining always below 10 as an acceptable criteria as shown in Table 4.

TABLE 4

| No. of Cells | RPM | Mean % Dissolution Release Rate (Minutes) | | | | | | |
|---|---|---|---|---|---|---|---|---|
| | | 15 | 20 | 30 | 45 | 60 | 75 | 90 |
| 6 | 120 | 36.8 | — | 79.2 | 92.0 | 95.7 | — | — |
| | | (4.4) | | (6.1) | (2.2) | (1.5) | | |
| 6 | 120 | 40.1 | — | 76.6 | 89.4 | 91.2 | — | — |
| | | (9.3) | | (6.7) | (4.3) | (3.1) | | |
| 6 | 120 | 41.1 | — | 71.3 | 84.7 | 90.5 | — | — |

TABLE 4-continued

| No. of Cells | RPM | Mean % Dissolution Release Rate (Minutes) | | | | | | |
|---|---|---|---|---|---|---|---|---|
| | | 15 | 20 | 30 | 45 | 60 | 75 | 90 |
| | | (7.4) | | (7.5) | (6.8) | (4.8) | | |

( ) = Standard Deviation

EXAMPLE 4

This Example illustrates the release rate of other suppository formulations containing the anti-arthritic drug of Example 1 using the procedure of Example 4. These formulations comprised magnesium stearate or magnesium stearate and aluminum hydroxide as excepients and either a suppository base containing 90.4% triglyceride and 10.1% diglyceride (Wecobee M) or a saponified oleic Acid base (Eutectol AM) as the base.

Table 5 summarizes the results.

TABLE 5

| Exp. No. | Base | Excipients | Mean % Drug Released (minutes) | | | |
|---|---|---|---|---|---|---|
| | | | 15 | 30 | 45 | 60 |
| 1 | Wecobee M | Mg Stearate | 18.6 | 35.0 | 50.3 | 65.3 |
| | | | (2.8) | (3.3) | (5.2) | (9.0) |
| 2 | Eutectol AM | Mg Stearate | 22.5 | 40.3 | 58.0 | 74.3 |
| | | | (1.4) | (3.2) | (5.7) | (4.0) |
| 3 | Wecobee M | Mg Stearate + Al(OH)$_3$ | 40.1 | 76.6 | 87.1 | 91.2 |
| | | | (9.3) | (6.7) | (4.3) | (3.1) |

The method, using the cell of the invention, shows that the differences in base and/or excipients in the suppository formulation affects the in-vitro dissolution release rate for the suppository.

What is claimed is:

1. A dissolution cell assembly for measuring the release rate of a drug comprising:
   a dissolution cell comprising
   (a) a rectangular top wall having a central opening therein;
   (b) a pair of trapezoidal side walls extending generally perpendicularly from said top wall;
   (c) a pair of end walls comprised of a mesh material and extending from said top wall, said end walls being attached to and disposed between said side walls; and
   (d) a bottom wall comprised of a mesh material attached to and extending between said end walls and said side walls;
   (e) closure means for closing said opening releasably attached about said opening; and means for attaching a shaft to said closure means for rotatably mounting said dissolution cell.

2. The dissolution cell of claim 1 wherein said top wall and said side walls are comprised of stainless steel.

3. The dissolution cell of claim 1 wherein said end walls and bottom wall are comprised of stainless steel wire mesh.

4. The dissolution cell of claim 1 wherein said end walls and said bottom wall are comprised of an integral strip of mesh material.

5. A dissolution cell assembly for measuring the release rate of a drug contained therein comprising:
   a dissolution cell comprising
   (a) a rectangular top wall having a central opening therein;
   (b) an extension member enclosing said opening and terminating in a flange;

(c) a pair of trapezoidal side walls extending generally perpendicularly from said top wall;
(d) a pair of end walls comprised of a mesh material and extending from said top wall, said end walls being attached to and disposed between said side walls; and
(e) a bottom wall comprised of a mesh material attached to and extending between said side walls and said end walls;
(f) closure means releasably attached to said extension member; and
means for attaching a shaft to said closure means for rotatably mounting said dissolution cell.

6. The dissolution cell of claim 5 wherein said end walls and bottom wall are comprised of a stainless steel wire mesh having a mesh size of 30 and a wire diameter of 0.013 inches.

7. The dissolution cell of claim 5 wherein said top wall and said side walls are comprised of stainless steel.

8. The dissolution cell of claim 5 wherein said end walls and said bottom wall are comprised of an integral strip of mesh material.

9. A method for the in-vitro determination of the release of a drug from a drug form comprising:
(a) placing said drug form in a dissolution cell of a dissolution cell assembly which comprises:
a dissolution cell comprising
  (i) a rectangular top wall having a central opening therein;
  (ii) a pair of trapezoidal side walls extending generally perpendicularly from said top wall;
  (iii) a pair of end walls comprised of a mesh material and extending from said top wall, said end walls being attached to and disposed between said side walls; and
  (iv) a bottom wall comprised of a mesh material attached to and extending between said end walls and said side walls;
  (v) closure means for closing said opening releasably attachable about said opening; and a shaft attached to and extending from said closure means;
(b) attaching said closure means about said opening to close said opening;
(c) mounting said shaft in a rotation means;
(d) placing said dissolution cell in a dissolution medium;
(e) rotating said rotation means to rotate said dissolution cell; and
(f) measuring the change in concentration of said drug released from said form at predetermined intervals.

10. The method of claim 9 wherein said dissolution cell assembly is rotated at about 120 rpm.

11. The method of claim 9 wherein said end walls and said bottom wall are comprised of stainless steel wire mesh having a mesh size of 30 and a wire diameter of 0.013 inches.

12. The method of claim 9 wherein said top wall and said side walls are comprised of stainless steel.

13. The method of claim 9 wherein said end walls and said bottom wall are comprised of an integral strip of mesh material.

* * * * *